United States Patent [19]

McConnell

[11] 4,357,827
[45] Nov. 9, 1982

[54] GRAVIMETRIC ABSORBENCY TESTER

[75] Inventor: Wesley J. McConnell, Wallingford, Pa.

[73] Assignee: Johnson & Johnson, New Brunswick, N.J.

[21] Appl. No.: 149,214

[22] Filed: May 12, 1980

[51] Int. Cl.³ .............................................. G01N 5/02
[52] U.S. Cl. ....................................... 73/73; 137/408
[58] Field of Search ....................... 73/73, 74, 76, 296; 137/408

[56] References Cited

U.S. PATENT DOCUMENTS

| 2,545,281 | 3/1951 | Hunt | 73/73 |
| 3,155,109 | 11/1964 | Anthon | 137/408 |
| 3,952,584 | 4/1976 | Lichstein | 73/73 |

FOREIGN PATENT DOCUMENTS

| 160386 | 5/1941 | Fed. Rep. of Germany | 73/296 |
| 129688 | 2/1978 | German Democratic Rep. | 73/73 |

OTHER PUBLICATIONS

Swedish Standards, 25-12-28, by Swedish Standards Commission: Standards Commitee For Textiles; Sep. 1971.

Primary Examiner—E. R. Kazenske
Assistant Examiner—Denis E. Corr
Attorney, Agent, or Firm—Alice O. Robertson; Charles J. Metz

[57] ABSTRACT

An apparatus for determining the weight of liquid flowing to or from a test site is described. The apparatus comprises, in combination:
 a vessel for containing liquid, the vessel being supported solely by a balance;
 an indicator for indicating the weight sensed by the balance;
 a test surface to receive a specimen to be tested, the test surface including the test site;
 a conduit operatively connecting the vessel to the test site for directing a flow of liquid between the vessel and test site;
 an adjuster for vertically positioning the test site;

Wherein the vessel is supported by the balance through a spring, which serves to maintain the surface of the liquid in the vessel at a constant elevation as liquid flows into and out of the vessel.

1 Claim, 6 Drawing Figures

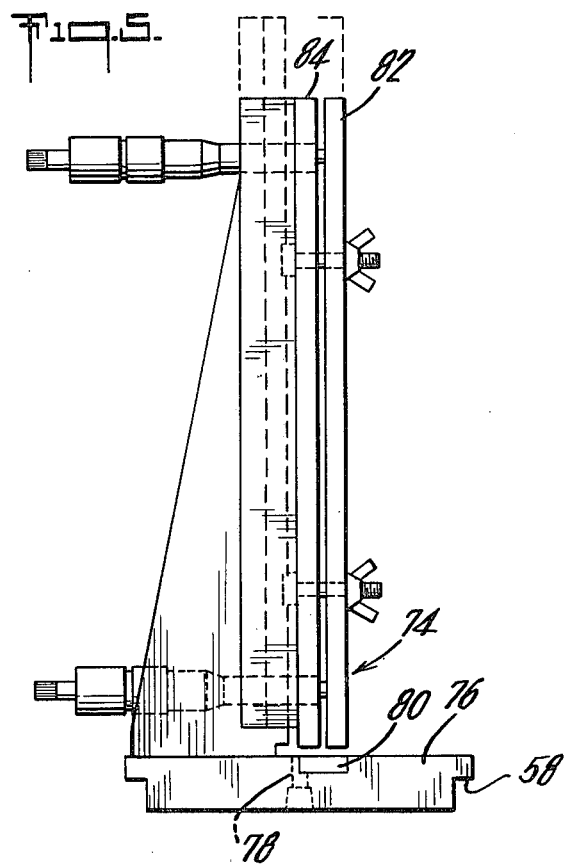
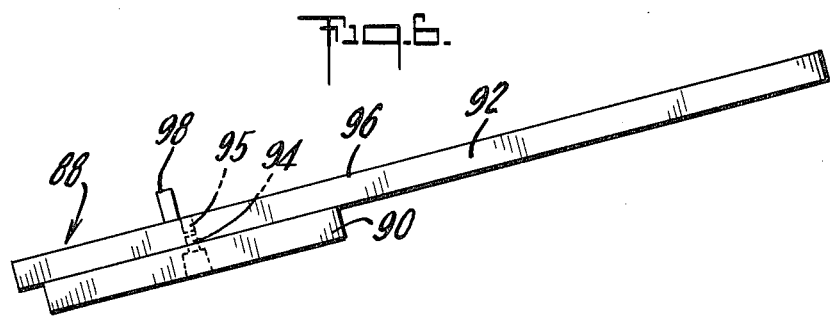

GRAVIMETRIC ABSORBENCY TESTER

The invention relates to an apparatus for determining the weight of liquid flowing to or from a test site.

BACKGROUND OF THE INVENTION

An instrument for reproducibly and accurately measuring the liquid absorbency and related properties of a material is useful in the arts relating to absorbent products. Such absorbent products include surgical dressings, disposable diapers, sanitary products, and the like. The present invention is addressed to just such an apparatus which not only provides accurate and reproducible results, but which is also quite versatile in that it can determine liquid absorbency and related properties in a number of different modes simulating different use conditions. The instrument can determine various properties, such as the total quantity of liquid retained by a product under loaded or no-load conditions, the rate at which liquid is taken up, and the rate at which liquid is expressed under load.

THE PRIOR ART

In East German Pat. No. 129,688, there is disclosed an absorbency tester for leather. The tester consists of a tube having an opening in the bottom which is fitted with a felt wick. The tube also has a stopcock at the top. The tube is filled with distilled water, weighed, placed on a movable carriage, and then laid on the surface of the leather to be tested so that the felt tip contacts the leather. A pressure weight is attached and the stopcock is opened. The carriage is moved over a predetermined distance for a selected number of times, the tap is then closed, and the test tube is reweighed. The weight difference indicates the amount of liquid taken up by the test sample. Hunt, in U.S. Pat. No. 2,545,281, describes a fabric moisture absorbency tester. The apparatus includes a vessel filled with water, a screen on the top of the vessel exactly even with the level of the surface of the water, and a capillary tube in contact with the vessel containing water, with the tube being held at the same level as the surface of the water. When a test specimen is pressed down on top of the screen, water is absorbed and is sucked out of the capillary tube.

Anthon, in U.S. Pat. No. 3,155,109, discloses a liquid supply apparatus in which a liquid level in a container is maintained at a constant head by spring means or equivalent resilient means that are constructed to raise the reservoir as the liquid is drawn off by a distance exactly equal to the distance the level drops in the reservoir.

Lichstein, in U.S. Pat. No. 3,952,584, discloses an absorbency tester that measures the volume of liquid absorbed by whatever hydrostatic head is desired.

BRIEF SUMMARY OF THE INVENTION

The invention provides an apparatus for determining the weight of liquid flowing to or from a test site which comprises, in combination:

A vessel for containing liquid, said vessel being supported solely by weighing means;

Indicating means for indicating the weight sensed by said weighing means;

A test surface to receive a specimen to be tested, said test surface including said test site;

Conduit means operatively connecting said vessel to said test site for directing a flow of liquid between said vessel and said test site; and Means for vertically positioning said test site.

By using this apparatus, the weight of liquid flowing from the vessel to the specimen at the test site or from the specimen back to the vessel, can be accurately determined.

BRIEF DESCRIPTION OF THE DRAWINGS

FIGS. 2 through 6 are sectional elevations of different test cells that can be employed with the apparatus of the invention.

DETAILED DESCRIPTION OF THE INVENTION

Figure 1:
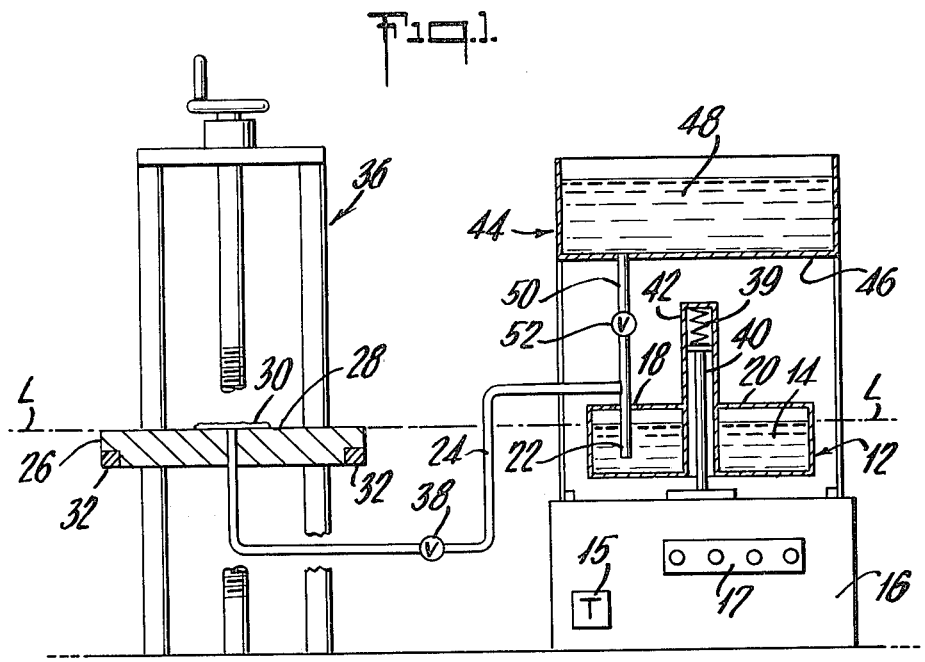
FIG. 1 is a front elevation, partly schematic, of an apparatus embodying the principles of the invention.

Referring first to FIG. 1, in which a partially schematic, front elevation of a preferred form of the apparatus of the invention is shown, the apparatus includes a vessel 12 which acts as a reservoir for the liquid 14 to be employed in testing the performance of a suitable sample 30. The vessel 12 is supported solely by the weight sensing surface of weighing means such as an electronic balance 16 having a tare switch 15 and a display 17. (If desired, the weighing means can be a force transducer or similar device, instead of a balance.) The vessel 12 is preferably a closed vessel having a hole 18 in the top 20 through which a siphon tube 22 may be lowered. The liquid 14 is introduced into the vessel 12 to a predetermined level "L". A siphon tube 22 is inserted through the hole 18 in the top 20 of the vessel 12 so that it extends down into the liquid 14. The siphon tube 22 is connected by tubing 24 to a test cell 26.

The test cell 26 has a surface 28 for receiving the specimen 30 to be tested. As shown in FIG. 1, the test cell 26 is a flat, disk-shaped plate having a hole through its center, although it could have other configurations, such as will be explained in more detail below. The siphon tube 22 is connected by tubing 24 to the bottom of the test cell 26 so that liquid flowing through the siphon tube 22 can flow up through the test cell 26 to the test specimen 30. The test cell 26 is mounted on an "O"-shaped support 32 such that the top surface 28 of the test cell 26 is exactly in the same horizontal plane "L" as the surface 34 of the liquid 14 in the reservoir vessel 12. In order to adjust the vertical position of the test cell 26, the test cell support 32 is attached to an adjustable jack 36 or similar means. By maintaining the top surface 28 of the test cell 26 in the same horizontal plane "L" as the surface 34 of the liquid 14 in the vessel 12, a zero hydrostatic head is then maintained between the reservoir of liquid 14 and the top surface 28 of the test cell 26. The jack 36 permits testing at various hydrostatic heads as may be needed or desired.

In operation, the specimen 30 to be tested is placed on the top surface 28 of the test cell 26, a valve 38 in the tubing 24 is opened so that liquid 14 is free to flow from the vessel 12 to the test cell 26. The specimen 30 then absorbs liquid 14 from the reservoir vessel 12. By noting the weight of the vessel 12 before any liquid 14 has flowed from the vessel 12 to the specimen 30, and the weight after all absorption by the specimen 30 has ceased, the total amount of liquid taken up by the test specimen 30 is then determined. The apparatus can also be employed to evaluate the absorbency rate of a specimen by noting the weight change over a period of time.

A preferred liquid reservoir vessel 12 arrangement is shown in FIG. 1. The vessel 12 is mounted on the balance 16 by means of a leveling spring 39 and a mounting pin 40. The mounting pin 40 on the balance 16 is adapted to fit into a mounting tube 42 in the center of the vessel 12.

The mounting tube 42 contains a spring 39 which, when the vessel 12 is in place on the mounting pin 40, is compressed between the top of the pin 40 and the top of the mounting tube 42. By appropriate selection of the compression strength of the spring 39, the vessel 12 will remain at a constant elevation as liquid 14 flows out of or back into the vessel 12. With a vessel constructed so that the area of the surface of the liquid remains constant with changes in liquid level, the required spring constant can be calculated by multiplying the density of the test liquid by the area of the liquid surface.

FIG. 1 also shows a preferred design of a reserve tank 44 that is constructed to fit over the vessel 12, but without touching the vessel 12 and without impinging on the weight sensing surface of the balance 16. The reserve tank 44 contains a reserve compartment 46 for containing reserve quantities 48 of the liquid. In the bottom of the reserve compartment 46 is an outflow conduit 50 through which liquid 48 can flow into the vessel 12. An outflow valve 52 is included in the conduit 50 to control the flow of liquid.

Figure 2:
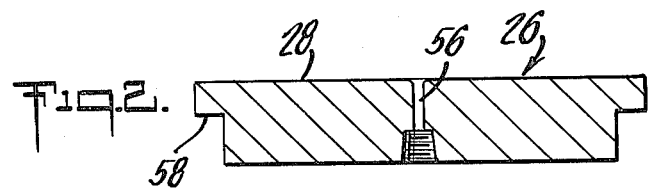

A variety of different types of test cells can be employed. For instance, FIGS. 1 and 2 show a test cell 26 that can be employed to evaluate the radial wicking characteristics of a test specimen 30. The cell 26 for this purpose consists simply of a flat, disk-shaped plate having a hole 56 in the center through which liquid can flow up to the test specimen. A flange 58 is provided in the lower periphery of the test cell 26 so that the cell 26 will fit into the ring-shaped support 32.

Figure 3:
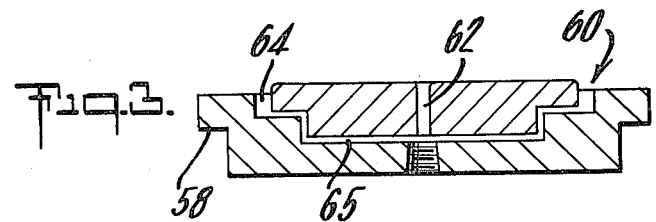

In FIG. 3 there is shown a test cell 60 for evaluating both radial wicking and desorption capability of the test specimen. This test cell 60 contains a hole 62 in the center similar to that in the test cell 26 shown in FIGS. 1 and 2, but is also contains a concentric trough 64 for receiving expressed liquid which may be generated when there is an increase in any compression load that is impressed on the test specimen while its absorbency performance is being tested. The trough 64 is connected to the central hole 62 by a conduit 65. The expressed liquid will flow back to the reservoir vessel 12 causing a change in weight of the vessel 12 plus liquid 14. These changes can be used to analyze the performance of the test specimen 30.

Figure 4:
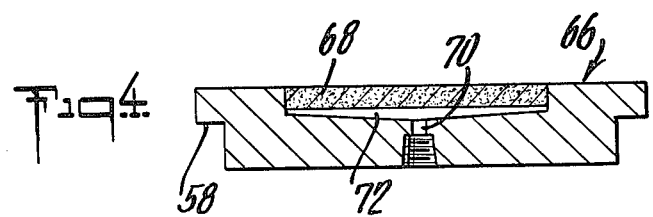

In FIG. 4 there is shown a test cell 66 which can be used to measure transverse wicking, or simply the wicking capability in one direction only. This test cell 66 contains a porous fritted glass plate 68 and is constructed to have a large proportion of the entire bottom of the fritted glass plate 68 in contact with the test liquid. This is accomplished by having the hole 70 through which liquid flows upwardly from the reservoir vessel 12 open up into a hollow chamber 72 just under the porous fritted glass plate 68. After a test specimen has been placed on the porous plate 68, the valve 38 (FIG. 1) is kept open during the test to keep the hollow chamber 72 full of liquid; otherwise, air may be drawn down through the plate 68 as the specimen absorbs liquid.

FIG. 5 shows a test cell 74 that can be used to test vertical wicking of a test specimen. The cell 74 contains a plate 76 similar to the cell 26 of FIGS. 1 and 2, except that the hole 78 in the center communicates with a transverse trough 80. A jig composed of two plates 82, 84 is permanently attached to the plate 76 and holds the test specimen (not shown) vertically over the trough 80 with the bottom edge of the test specimen slightly below the level of the liquid in the trough 80.

The test cell 74 shown in FIG. 5 can be employed in several different ways. First, the two plates 82, 84 can be set a distance apart such that the specimen can simply be suspended freely between them so that it may expand in both directions (i.e., toward each wall 82, 84) when it absorbs liquid. The plates 82, 84 can also be set a preselected distance apart so as to clamp the specimen between two rigid surfaces. Another alternative is to replace the rigid face of one of the walls 84 with a conformable membrane (not shown) with means (not shown) to impart a constant pressure behind the membrane. By so doing, a uniform pressure can be maintained on the specimen during testing.

FIG. 6 shows a test cell 88 that can be employed to test wicking of a specimen at any angle from the horizontal from 0° through 90°. The cell 88 contains a disk-shaped bottom plate 90 that just fits inside the O-shaped support 32 (FIG. 1), and an elongated top plate 92. A hole 94 through both plates 90, 92 delivers liquid to a specimen (not shown) supported by the top surface 96 of the top plate 92. An end of the specimen is in contact with a wall 98 that extends across the width of the top plate 92. Liquid flowing through the hole 94 fills a transverse trough 95 at the base of the wall 98 and then contracts the said end of the specimen. The wicking properties of the specimen can be evaluated at any angle from 0° through 90° by measuring the weight of liquid absorbed and/or the movement of the liquid front. The height of the test cell 88 is preferably adjusted so that the top of the trough 95 is slightly above the horizontal plane "L" of the top surface 34 of the liquid 14 in the reservoir vessel 12, per FIG. 1.

The support 32 (FIG. 1) for the test cells can be attached to the jack 36 in such a way that the support 32 and test cell can be rotated, with the center of rotation being the liquid delivery hole in the test cell surface. In this way, wicking at any angle between 0° and 90° can be evaluated, while maintaining the liquid delivery source on the surface of the test cell at a known vertical level coordinated with the level L of the liquid in the reservoir vessel 12.

A sample loading device may be employed in conjunction with the apparatus of the invention to impress a preselected compression load or weight on the specimen while it is being tested. Such a loading device is described in U.S. patent application Ser. No. 149216 filed on the same day as this application, now U.S. Pat. No. 4,314,482, entitled "Sample Loading Device", by Theodore J. Krainski, Jr., and assigned to the same assignee as this application, the disclosure of which is incorporated herein by reference.

What is claimed is:

1. An apparatus which comprises:
    (a) a closed vessel for containing liquid;
    (b) a weighing means for sensing change in weight of liquid contained in said vessel and further supporting said vessel;
    (c) an indicating means for indicating the weight sensed by said weighing means;
    (d) a test surface to receive a specimen to be tested said test surface being part of an interchangeable test cell;
    (e) a conduit means opertively connecting said vessel to said test cell for directing a flow of liquid between said vessel and said test cell;

(f) a mechanical means for vertically positioning said test cell, said mechanical means including a support for said test cell and further provided with a means to rotatively adjust the test cell to any desired angle between 0° and 90°;

(g) a means to maintain the surface of liquid contained in said vessel at a substantially constant elevation as liquid flows out of or into said vessel, said maintaining means being a leveling spring mounted on a pin and fitted in a mounting tube positioned in the center of said vessel, said pin further comprising means by which the vessel is mounted on the weighing means, whereby the weight of liquid flowing from said vessel to said test cell or from said test cell to said vessel, can be determined.

* * * * *